1
United States Patent [19]

Beckman et al.

[11] Patent Number: 4,933,404

[45] Date of Patent: Jun. 12, 1990

[54] PROCESSES FOR MICROEMULSION POLYMERIZATION EMPLOYING NOVEL MICROEMULSION SYSTEMS

[75] Inventors: Eric J. Beckman, Kennewick; Richard D. Smith; John L. Fulton, both of Richland, all of Wash.

[73] Assignee: Battelle Memorial Institute, Richland, Wash.

[21] Appl. No.: 274,596

[22] Filed: Nov. 22, 1988

Related U.S. Application Data

[63] Continuation of Ser. No. 125,842, Nov. 27, 1987, abandoned, and Ser. No. 152,256, Feb. 4, 1988.

[51] Int. Cl.$^5$ ............................................. C08F 2/00
[52] U.S. Cl. .................................. 526/207; 526/303.1; 526/317.1; 526/240; 526/264; 526/319
[58] Field of Search ........................................ 526/207

[56] References Cited

U.S. PATENT DOCUMENTS

| | | | |
|---|---|---|---|
| 2,586,322 | 2/1952 | Franta | 526/207 |
| 2,982,749 | 5/1961 | Friedrich et al. | 260/23 |
| 3,265,642 | 8/1966 | Hatano et al. | 526/207 |
| 3,284,393 | 11/1966 | Vanderhoff et al. | 526/207 |
| 3,522,228 | 7/1970 | Fukui et al. | 260/94.9 |
| 3,836,512 | 9/1974 | Chu | 526/207 |
| 3,915,921 | 10/1975 | Schlatzer, Jr. | 260/78.5 R |
| 3,957,739 | 5/1976 | Cabestany et al. | 526/207 |

OTHER PUBLICATIONS

"Organized Molecular Assemblies in the Gas Phase: . . . ", Gale et al. Journal of the American Chemical Society 1987, 109 pp. 920, 921.

"In Inverse Microemulsion", Candau et al. Polymer Chemistry Edition vol. 23, 193–214 (1985).

"Technological Relevance of Microemulsions and Reverse Micelles in Apolar Media", Langevin pp. 287-303-75231 Paris Cedex 05.

"Reverse Micelle and Microemulsion Phases in Supercritical Fluids", Fulton et al, The Journal of Physical Chemistry, 1988, 92, 2903–2907.

"Reverse Micelle Supercritical Fluid Separations", Smith et al. Chemical Sciences Dept. Richland, Washington 99352.

*Primary Examiner*—Joseph L. Schofer
*Assistant Examiner*—N. Sarofim
*Attorney, Agent, or Firm*—Marger & Johnson, Inc.

[57] ABSTRACT

This invention is directed to a microemulsion system comprising a first phase including a low-polarity fluid material which is a gas at standard temperature and pressure, and which has a cloud-point density. It also includes a second phase including a polar fluid, typically water, a monomer, preferably a monomer soluble in the polar fluid, and a microemulsion promoter for facilitating the formation of micelles including the monomer in the system. In the subject process, micelles including the monomer are formed in the first phase. A polymerization initiator is introduced into the micelles in the microemulsion system. The monomer is then polymerized in the micelles, preferably in the core of the micelle, to produce a polymeric material having a relatively high molecular weight.

40 Claims, 6 Drawing Sheets

PROCESSES FOR MICROEMULSION POLYMERIZATION EMPLOYING NOVEL MICROEMULSION SYSTEMS

This invention was made with United States Government support, and the Government has rights therein under Contract No. 2511006937 with the Department of the Army.

RELATED APPLICATIONS

This is a continuation of pending related applications U.S. Ser. No. 07/125,842, filed Nov. 27, 1987 now abandoned and U.S. Ser. No. 07/152,256, filed Feb. 4, 1988, which are assigned to a common assignee, Battelle Memorial Institute.

BACKGROUND OF THE INVENTION

This invention relates to methods for the polymerization of monomers, and to novel microemulsion systems for conducting such polymerizations.

Emulsion polymerization is an important commercial process because, in contrast to the same free-radical polymerization performed in the bulk, molecular weight and reaction rate can be increased simultaneously.[1] Furthermore, the lower viscosity of an emulsion system compared to that of the corresponding bulk process provides better control over heat transfer. Commercial emulsion processes usually use a surfactant-water-monomer system which is stabilized by vigorous stirring. The dispersed phase contains micelles, approximately 10 to 50 nm in diameter, as well as monomer droplets. In the absence of agitation, these monomer droplets will coagulate and separate as a second phase. If, as is the usual practice,[1] a continuous-phase soluble initiator is used, polymerization commences at the micelle interface and proceeds within the micelles. During the reaction, monomer diffuses from the large droplets into the micelles. Exhaustion of these monomer reservoirs signals the end of the polymerization.

Recently,[2,20,21] polymerization in microemulsions has been studied. In contrast to the emulsion system described above, a microemulsion is thermodynamically stable, and thus one-phase and optically clear in the absence of agitation. Microemulsion polymerization has been used to produce stable lattices with a very fine (approx. 50 nm) particle size.[4]

Most emulsion polymerization systems employ an oil-soluble monomer dispersed in an aqueous continuous phase. Recent work[2-8] describes polymerizing water-soluble monomers in an inverse emulsion (a water in oil emulsion). However, conventional inverse emulsions are even less stable than conventional water-in-oil emulsions,[1]. Although an inverse microemulsion polymerization is an efficient way to produce high molecular weight polymer, there remains the problem of separation of the polymer from a large volume of oil.

SUMMARY OF THE INVENTION

The processes and systems relating to microemulsions of the present invention overcomes the above problems associated with the prior art, and more particularly provide processes and systems for polymerizing a monomer, in which a microemulsion system is formed and employed.

The microemulsion system comprises a first phase including a low-polarity fluid material which is a gas at standard temperature and pressure, and which has a cloud-point density. It also includes a second phase including a polar fluid, typically water, a monomer, preferably a monomer soluble in the polar fluid, and a microemulsion promoter for facilitating the formation of micelles including the monomer in the system. In the subject process, micelles including the monomer are formed in the first phase.

A polymerization initiator is introduced into the micelles in the microemulsion system. The monomer is then polymerized in the micelles, preferably in the core of the micelle, to produce a polymeric material having a relatively high molecular weight. More specifically, polymeric product material preferably has a weight average molecular weight of at least about 100,000, and more preferably at least about 200,000. Preferably, the weight average molecular weight can be up to about 1,000,000, and more preferably up to at about 2,000,000, and most preferably up to about 5,000,000.

Moreover, the weight average molecular weight of the polymeric material polymerized at a temperature about the supercritical temperature of the fluid material is preferably at least 25%, more preferably at least 50%, and most preferably at least 100% greater than the weight average molecular weight of the polymeric material produced under substantially the same reaction conditions except that the polymerization is conducted at a temperature below the supercritical temperature of the fluid material. Supercritical fluids, materials at temperatures and pressures above their critical values, display physical properties which are intermediate to those of liquids and gases.[9] The density of a supercritical fluid, and consequently the whole range of density-dependent properties (viscosity, solvent power, dielectric constant, etc.) can be readily varied over more than an order of magnitude by varying pressure.

The microemulsion system of the present invention preferably comprises a substantially stable inverse emulsion which includes a first phase comprising a substantially discontinuous phase and a second phase comprising a substantially continuous phase. The system can be maintained at a pressure and temperature such the density of the low-polarity fluid exceeds its cloud-point density thereof. Moreover, the polymerization is preferably conducted at a temperature which is at least equal to the supercritical temperature of the low-polarity fluid material.

The process of the present invention typically employs a water-soluble monomer. This water-soluble monomer generally comprises at least one of acrylamide, methacrylamide, acrylic acid, methacrylic acid, an acrylic acid salt, vinyl pyrolidone, and vinyl acetate. However, the acrylamide and methacrylamide monomers are most preferred.

The subject microemulsion promoter generally comprises a surfactant. Particularly, the microemulsion promoter is one which is substantially soluble in the second phase. The microemulsion promoter preferably comprises at least one of a non-ionic surfactant and an anionic surfactant. Moreover, a non-ionic surfactant can be chosen which has an HLB of from about 5 to 10, preferably 6 to 8, and most preferably from 6.5 to 7.5. Furthermore, in some instances, the monomer can act as a microemulsion co-promoter. Typically this occurs when such a co-promoter is a water-soluble monomer in the first phase.

It is preferred that the molar ratio of the microemulsion promoter to the polar fluid is at least about 1, more preferably at least about 3, and most preferably at least about 5. It is also preferred that the microemulsion promoter chosen so that it substantially solubilizes the polar fluid at pressures up to about 500 bar.

The low-polarity fluid is preferably a non-polar fluid. The non-polar fluid material is preferably at least one lower alkane. More preferably, the fluid material is a lower alkane which is one of ethane, propane and butane.

The process typically includes a polymerization initiator capable of passing through the continuous phase into the discontinuous phase for catalyzing the polymerization of the monomer within the interstices of the micelles. The polymerization initiator is typically activated by at least one of thermal and radiation means. Furthermore, the polymerization initiator preferably comprises at least one of an azo, peroxide, and disulfide initiator compound.

Unexpectedly, in the process of the present invention, the pressure required to form the microemulsion system can be reduced as the amount of the first phase in the microemulsion system is increased. The volume fraction dispersal phase in the microemulsion system is defined as the total volume of the microemulsion promoter, the polar fluid and the monomer as a fraction of the total volume of the microemulsion system. As the volume fraction dispersed phase increases up to about 0.30, the clearing pressure is measured at various intervals by comparing the difference in pressure values at a volume fraction dispersed phase (VPFP) of 0.10 with pressure valve at a VPFP of 0.15 to 0.03, dividing that value by the VPFP at 0.10, and multiplying that quantity by 100, the reduction in pressure was at least 20%, more preferably at least 25%, and most preferably at least 30%.

The foregoing and other objects, features and advantages of the invention will become more readily apparent from the following detailed description of a preferred embodiment which proceeds with reference to the drawings.

DETAILED DESCRIPTION OF PREFERRED EMBODIMENTS

Figure 1:
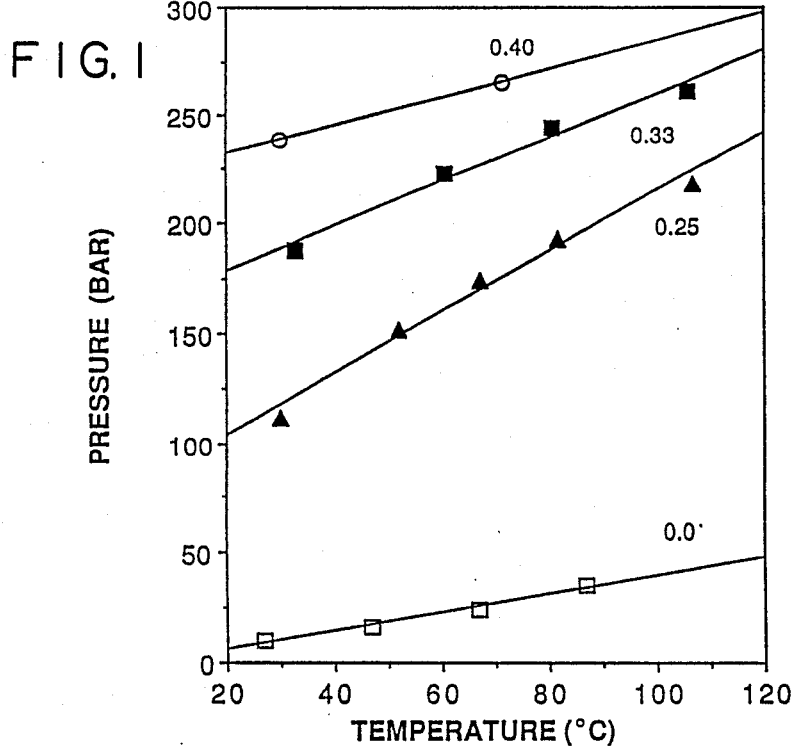
FIG. 1 is a graphical representation of cloud point curves of an anionic surfactant (AOT) and a supercritical fluid (propane) system with a water to surfactant ratio (W) of 5.0 for monomer (acrylamide) to surfactant ratios up to 0.40. (See Table 1 for data.)

Referring to FIGS. 1-11, various properties of the microemulsion system of the present invention are graphically represented which define certain relationships between the components forming the subject system. Exemplary component materials were used in these experiments to produce the data which forms such graphical representations. Such materials include non-ionic surfactants Brij 52 (B52) and Brij 30 (B30) which were obtained from the Sigma Chemical Company and used as received. Although nominally $C_{16}E_2$ and $C_{12}E_4$, respectively, these surfactants are each composed of a mixture of species of differing chain lengths. Furthermore, Aerosol AOT, i.e., sodium bis(2-ethyl hexyl) sulfosuccinate, was obtained from Fluka Chemical (purum grade) and purified according to Kotlarchyk, et al.[11] Acrylamide (AM) was obtained from the Aldrich Chemical Company (Gold Label 99+%) and recrystallized twice from chloroform. Water was doubly de-ionized. Propane was obtained from Union Carbide Linde Division (CP Grade), ethane from Air Products (CP Grade), and all were used without further purification.

Phase transitions were observed visually using a high pressure view cell (volume=47 cm$^3$), capable of pressures to 600 bar, whose design has been previously described.[10] Material was introduced to the magnetically stirred call which was then sealed and pressurized with the fluid of choice using a Varian 8500 syringe pump. Gas mixtures were prepared by weight (composition ±.25%) in a 400 cm$^3$ lecture bottle, stirred for 15 minutes, then transferred to the syringe pump head. Temperature in the cell was controlled to within 0.1° C. using an Omega thermocouple-temperature programmer. Pressure was measured using a Precise Sensor 0 to 10,000 psi transducer and readout calibrated to within ±10 psi using a Heise Bourdon-tube gauge.

Regarding the microemulsion of this invention, the most efficient surfactant for the polymerization of a particular monomer is a function of the choice of the continuous phase, the monomer structure, and the polar solvent content. The correct choice is not necessarily apparent, particularly in the case where the continuous phase is a supercritical fluid. A study of the inverse emulsion polymerization of acrylamide (AM) within a toluene continuous phase,[14] below the cloud point density of toluene, showed that acrylamide acts as a co-surfactant with AOT.

However, since the critical temperature of aromatic hydrocarbons benzene and toluene are about 250°–300° C., the surfactant would be thermally destroyed if such polymerization were conducted about that Tc. In the AOT/water/propane system, of the present invention, the addition of small amounts of acrylamide significantly reduces the size of the one-phase region (see FIG. 1). By contrast, in the absence of acrylamide, a stable microemulsion at a water/surfactant ratio of 5 can be formed at pressures as low as 10 bar in propane (at 25° C.). For AM to function as a co-surfactant, it should partition preferentially to the interface. In the AOT/toluene system, the attraction of the AM for the AOT head group, the toluene continuous phase, and the surfactant tails is therefore assumed to be appropriately balanced. In the AOT/alkane system, the AM is apparently biased towards the AOT headgroup (solubility of AM in alkanes is extremely low)[12] and thus may remain largely associated with the core region.

In addition to the effects upon phase behavior, the presence of AOT, despite purification, initiates polymerization in acrylamide. Thus, while AOT has been the subject of numerous studies of reverse micelles in both sub- and supercritical fluids, it was not considered the best choice for acrylamide-containing micelles in an alkane continuous phase.

The empirical HLB process[15,16] was used to guide selection of an appropriate non-ionic surfactant. HLB, a means by which to categorize nonionic surfactants, normalizes the weight fraction of hydrophilic groups in a molecule to a 0 to 20 scale. While HLB is usually calculated from the surfactant structure alone, the behavior of a surfactant in an emulsion is governed by the continuous phase composition and monomer concentration as well.[17,22] This is because the emulsion stability depends on the proper balance of lipophile-oil and hydrophile-water interactions.[38] In addition, as mentioned above, acrylamide can act as a cosurfactant when particular oil-surfactant combinations are used. Preliminary screening of mixtures of the Brij 52 and Brij 30 (B52/B30) nonionic surfactants (which cover an HLB range of approximately 6 to 12) in non-supercritical pentane/AM/water system at atmospheric pressure showed the highest allowable AM concentrations were attained at an 80/20 ratio of the surfactants, a calculated HLB value of approximately 7.5. Similar results were obtained in liquid propane at 25° C. and 50 bar.

To maximize the amount of product yielded by inverse emulsion polymerization, it would be desirable to solubilize as much acrylamide as possible in the microemulsion while using the minimum amount of surfactant. Because water is merely a solvent which must eventually be removed from the product, the ideal water content of the microemulsion would be zero.

The solubility of either acrylamide or water in ethane/propane mixtures is extremely low.[12,13] The solubility of the surfactant mixture B52/B30 is also low. However, mixing acrylamide with the B52/B30 blend allows significantly larger amounts of both components to be solubilized in the alkane continuous phase so that the acrylamide monomer is a co-surfactant in this system. The B52/B30 mixture will solubilize acrylamide up to a AM:molar ratio of 1:4; larger ratios of AM lead to precipitation of an apparently solid phase. This acrylamide concentration is lower by a factor of 5 to 10 than that used by Leong and Candau[2] in the inverse microemulsion polymerization of acrylamide within a toluene continuous phase.

The addition of water significantly increases the amount of acrylamide which can be solubilized by the B52/B30/ethane/propane system. Accurate determination of cloud point curves of microemulsions with AM levels higher than 1.5 is difficult since the reddish-purple color which is evident upon clearing (see previous section) darkens significantly as the acrylamide level increases.

Although water allows for greater uptake of acrylamide by the microemulsion, water alone (AM=0) will not produce a one-phase system with the Brij 52/30 blend in an ethane/propane continuous phase. Acrylamide behaves as a co-surfactant with the B52/B30 blend, as evidenced by the results in FIG. 6. When more than the maximum allowable water level is added at a particular AM content, the system becomes turbid followed by the appearance of small droplets on the view cell windows (i.e., phase separation). Co-surfactant behavior by acrylamide depends both on the choice of continuous phase and primary surfactant structure.

Figure 6:
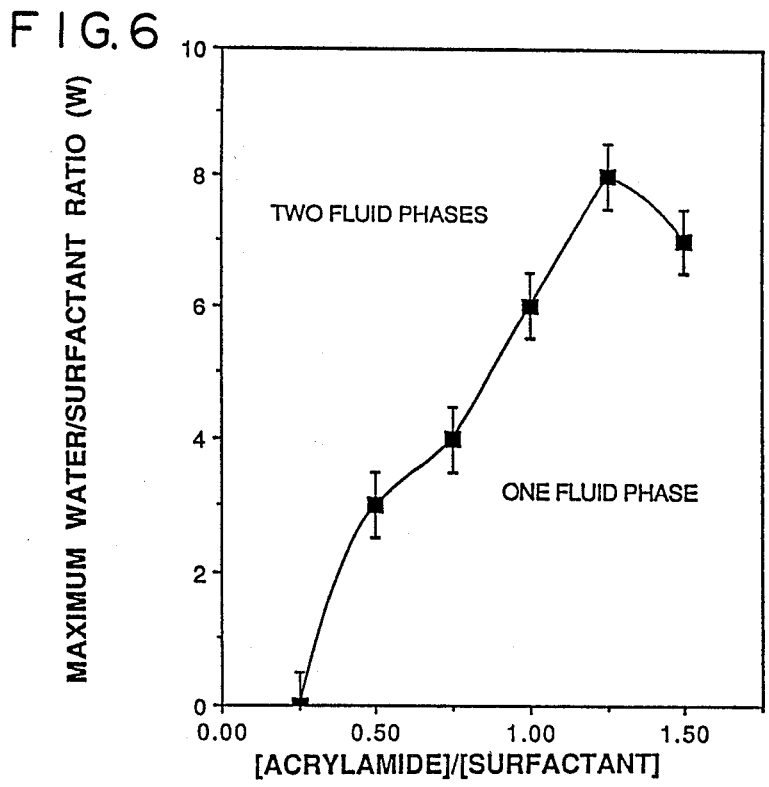
FIG. 6 is a graphical representation of a water to non-ionic surfactant (B52/B30) ratio of 80.4/19.6 with a supercritical fluid (ethane-propane) mixture at 30C and 500 bar versus monomer (acrylamide) to surfactant ratio. (See Table 6 for data.)

As the water concentration is raised at constant AM ratio, the clearing pressure decreases. The decrease is approximately 10 to 15 bar for each increase of 1.0 in the water/surfactant ratio up to the maximum water ratio as shown in FIG. 6.

In the application of these microemulsion systems to polymerization processes, it would be desirable to maximize polymer yield, which can be accomplished by maximizing the acrylamide ratio at constant surfactant loading. In addition, of course, the acrylamide ratio (as well as the water ratio) to the surfactant can be fixed and the total amount of surfactant in the system increased. Therefore, the effect of total dispersed phase concentration on the phase behavior was investigated. The dispersed phase concentration (the volume dispersed fraction) is equal to the total volume of surfactants+monomer+water divided by the total volume.

Figure 7:
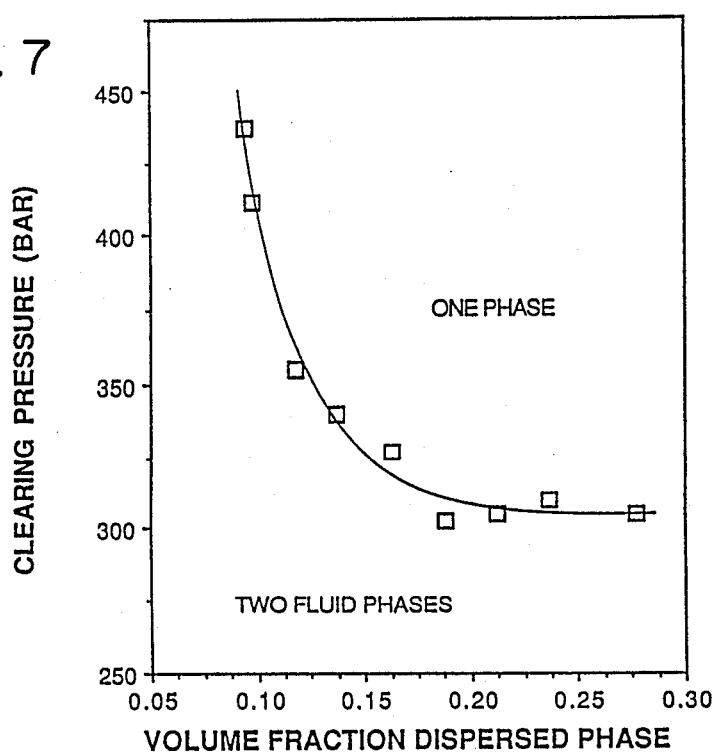
FIG. 7 is a graphical representation of the cloud point of non-ionic surfactant (B52/B30) in 80.4/19.6 supercritical fluid (ethane-propane) mixtures with a water to surfactant ratio of 5.0 and a monomer (acrylamide) to surfactant ratio of 1.0 versus dispersed phase volume fraction

Results shown in FIG. 7 reveal that increasing the dispersed phase volume fraction significantly reduces the pressure required to form a stable microemulsion. At a volume fraction of 0.09, a one phase system will not form at any pressure up to 550 bar, whereas increasing volume fraction to 0.15 will produce a stable microemulsion at less than 300 bar. Apparently, specific interactions between micelles contribute to this effect, as shown by the cloud point curves in FIGS. 8 and 9.

If the temperature is increased to a certain point, these microemulsion systems will remain turbid above the pressure at which they become one phase. This ceiling temperature decreases as the dispersed phase volume fraction increases (see FIG. 10). Apparently, a certain degree of micelle-micelle interaction is useful in improving the stability of this microemulsion (FIGS. 7-9) but if such interactions become too strong, as by raising the temperature as shown in FIG. 10, clustering and finally phase separation can occur. Thus a proper balance between micelle-micelle and micelle-continuous phase interactions must be achieved for maximum stability.

In order to broaden the temperature range in which a microemulsion acrylamide polymerization could be conducted within a supercritical alkane continuous phase, the phase behavior of the Brij mixture/water-/AM system in mixtures of propane ($T_c=97°$ C.) and ethane ($T_c=32°$ C.) was investigated, The ethane/propane mixture displays near-ideal mixture behavior[13,19] as evidenced by the linearity in the critical temperature-concentration curve in FIG. 6. In this series of experiments the water concentration was fixed at W=5.0 and that for the acrylamide at 1.0 (water and acrylamide concentrations are reported as molar ratios to the surfactants; the nominal molecular weights of 330 for Brij 52 and 360 for Brij 30 were used. The volume fraction of the dispersed phase (volume of surfactants+water+acrylamide divided by the total system volume) in this series of experiments was 0.136.

Figure 5:
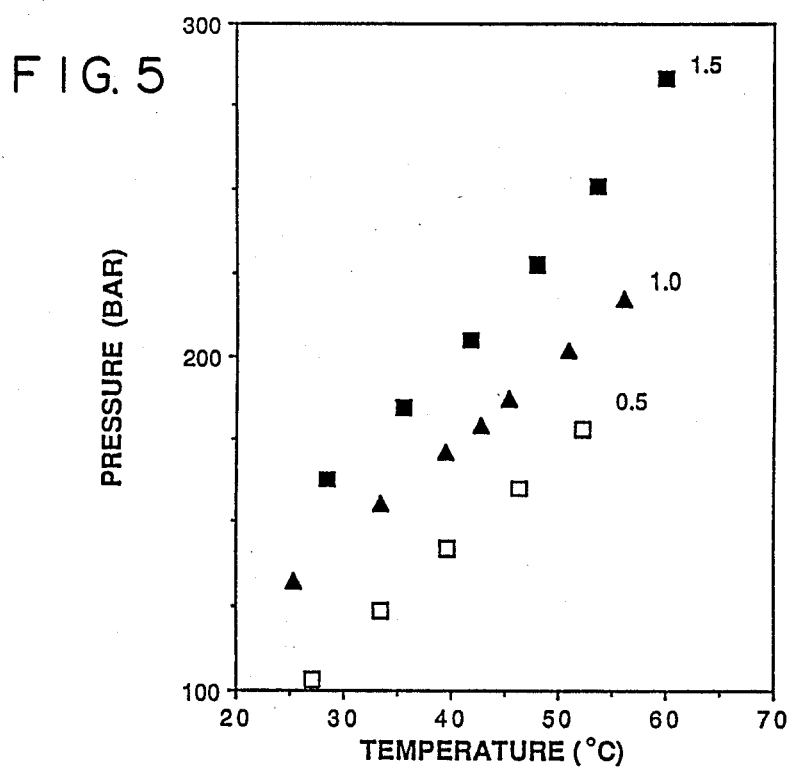
FIG. 5 is a graphical representation of the solubility of an 80/20 by weight non-ionic surfactant (B52/B30) mixture in an 80.4/19.6 supercritical fluid (ethane-propane) blend at 500 bar versus temperature. (See Table 5 for data.)

The phase behavior in FIG. 5 is given in terms of clearing points (or cloud points where the one phase region is above each curve), i.e., the pressure where the system becomes one phase was determined. Clearing points for the system under investigation here can easily be determined to within 1-2 bar using the view cell. As the pressure in the view cell is raised to the clearing point, the B52/B30/AM/water system turns from opaque to a transparent reddish-purple color. As pressure is increased beyond the clearing point, the color changes progressively to red-orange to orange to yellow (the color changes are reversible).

Figure 8:
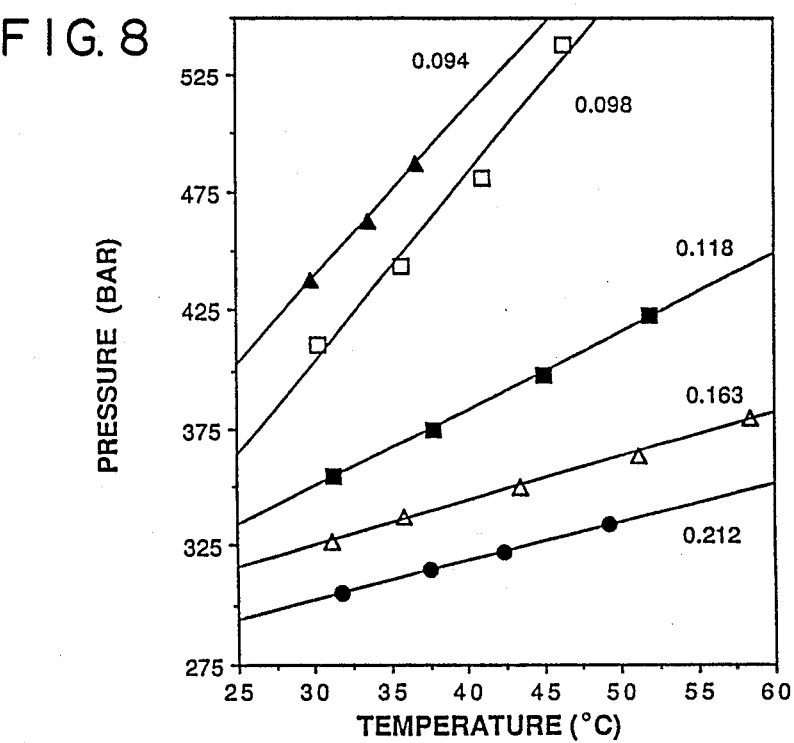
FIG. 8 is a graphical representation of cloud point curves of non-ionic surfactant (B52/B30) in 80.4/19.6 supercritical fluid (ethane-propane) mixtures with a water to surfactant ratio of 5.0 and a monomer (acrylamide) to surfactant ratio of 1.0 at five dispersed phase volume fractions.

The cloud point data in FIG. 8 reveal a series of curves which are essentially parallel and shifted to higher pressures as the amount of ethane in the mixture increases. These data are replotted as cloud point density versus temperature in FIG. 9. Densities for pure ethane and propane were taken from the literature, those for the 80.4/19.6 mixture were measured, and those for the other mixtures were calculated using the Starling variant of the Benedict-Webb-Rubin equation of state with literature values for the ethane and propane parameters.[18])

FIG. 6 also suggests that increasing the temperature increases the stability of the emulsion since the continuous phase density at the clearing point decreases. However, this trend does not continue indefinitely; above 72° C. this system is one phase yet turbid. Decreasing stability of microemulsions as temperature increases has been observed frequently in systems at atmospheric pressure.[23-24.]

These data show that for these lower alkanes it is the bulk property of continuous phase density rather than the structure of the fluid, that governs the phase behavior of the surfactant mixture/AM/water/ethane/propane system. Thus, a microemulsion polymerization reaction can be performed in these systems over a wide range in temperature, yet close to the continuous phase critical point, by varying the amount of ethane in the mixture (see FIGS. 2-4).

One of the independent variables is the choice of initiator, and consequently, the polymerization temperature. Initiation in a true inverse emulsion or microemulsion polymerization occurs in the continuous phase, usually due to degradation of an oil-soluble compound. The rate at which these compounds produce radicals is temperature-dependent. A variety of free-radical initiators are available thus allowing reaction to proceed at a reasonable rate at temperatures from 50° to 120° C. However, trace oxygen will prompt thermal initiation at higher temperatures, which, in the interests of good control over the reaction, is undesirable. Application of radiation will permit a fast reaction at lower temperatures, and can even preclude the need for a chemical initiator, but again could lead to initiation at sites other than in the continuous phase. Therefore, the initiator azo bisisobutyrnitrile (AIBN), which is usually used at temperatures between 50° and 70° C.,[1] was chosen. In order to obtain the process advantages inherent in using a supercritical continuous phase while minimizing the required operating pressure, it would be desirable to run the polymerization reaction as close to the critical temperature of the fluid as possible. Fortunately, rather than searching for a fluid with a critical temperature in the 50°-70° C. range, a mixture of ethane and propane can be used. The phase behavior of this microemulsion system in ethane/propane mixtures appears to depend on the fluid density, and not on the fluid structure. If the polymerization is to be run in the temperature range of 50°-70° C., while remaining approximately 5° C. above the continuous phase $T_c$, the alkane mixture should be 50 to 80 weight percent ethane (see FIG. 6).

Setting the reaction temperature will also determine the maximum dispersed phase volume fraction which will permit a transparent, stable microemulsion. As shown in FIG. 12, the ceiling temperature for stability of this microemulsion system decreases sharply as the dispersed phase volume fraction is increased. The minimum dispersed phase volume fraction is set by the selection of the maximum operating pressure allowed for a given reaction vessel. Results in FIG. 7 show the surprising result that the clearing pressure for this microemulsion system increases rapidly below approximately 10%. Thus, once the maximum and minimum volume fractions are set, the actual volume fraction for the reaction can be chosen, and thus the operating pressure range (between the clearing pressure and the safe maximum for the reaction vessel).

Figure 11:
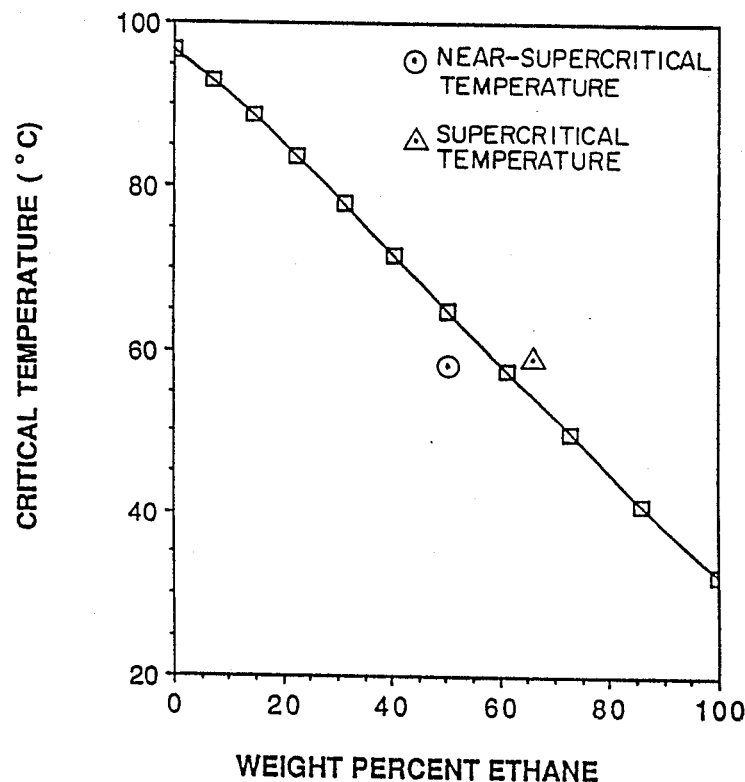
FIG. 11 is the graphical representation of FIG. 2 including points representing the ethane-propane mixture levels employed in the experiments set forth in Example 1.

The selection of acrylamide and water concentrations are also regulated by the phase behavior. Because acrylamide is a cosurfactant in the non-ionic surfactant-water-ethane/propane system, as the acrylamide is consumed during the polymerization, a point may be reached where the microemulsion will become turbid and begin to phase-separate. This situation can be postponed by setting the acrylamide ratio to 1.25, which is at the maximum of the AM-water curve (FIG. 11).

EXAMPLE 1

Experiments were conducted in which an acrylamide monomer was polymerized according to the process of the present invention, under the same reaction conditions, except at different ethane to propane ratios. This resulted in one experiment being conducted above the supercritical temperature of ethane-propane mixture and the other experiment being conducted at near the supercritical temperature of the ethane-propane mixture. Clearly, both reactions exceeded the cloud point density of the ethane-propane low-polarity fluid mixture.

The experimental procedure for each of these processes is as follows:

The processes were all run in a 47cc high pressure view cell at 60° C. 3.622 grams of Brij 52 and 0.904 grams of Brij 30 non-ionic surfactant were weighed out and then added to the cell. 1.2 grams each of water and acrylamide were then pre-mixed to the proper proportions and added as a solution to the cell. Thus, a solution was employed which was comprised of 50/50 acrylamide water, at a water/surfactant mole ratio of 5.0, and an acrylamide/surfactant ratio of 1.25. This recipe gives a total dispersed phase volume fraction of 0.16.

The cell was then sealed and a valve opened, admitting a mixture of ethane/propane gas from a Varian syringe pump which was used to maintain the required pressure. The ethane/propane blends were mixed by weight in a 400 cc aluminum pressure vessel and then transferred to a Varian syringe pump. The temperature of the system was raised to 60° and a hand-operated syringe pump was used to inject a 2% solution in of AIBN initiator (azo-bis(isobutyrnitrile). The polymerization was conducted in about five hours.

More specifically, the experiments were conducted (see FIG. 11) at a pressure of about 5,550 psi and an initiator level of about 1.4 mg. In one experiment involving near-supercritical temperature conditions (64.5% ethane-35.6% propane), polyacrylamide at a weight-average molecular weight of about 265,000 was produced. In another experiment involving supercritical temperature conditions (51.1% ethane, 48.9% propane), polyacrylamide having a weight-average molecular weight of 575,000 was produced.

Therefore, by employing the process of the present invention, high molecular-weight polyacrylamides can be produced, and unexpectedly, extremely high molecular weight materials can be formed by the process of this invention at temperatures which exceed the supercritical temperatures of the ethane-propane mixture.

REFERENCES

1. Odian, G., *Principles of Polymerization*, John Wiley & Sons, N.Y., 1981.
2. Candau, F., Y. S. Leong, *J. Polym. Sci.—Polym. Chem. Ed.* 1985, 23 193.
3. Candau, F., Z. Zekhnini, J. P. Durand, *J. Coll. Int. Sci.* 1986, 114, 398.
4. Leong, Y. S., S. J. Candau, F. Candau, in *Surfactants in Solution, Vol. III*, Eds. K. L. Mittal, B. Lindman, Plenum Press, N.Y., 1983, p. 1897
5. Graillat, C., C. Pichot, A. Guyot, M. S. El Aasser, *J. Polym. Sci.—Polym. Chem. Ed.* 1986, 24, 427.
6. Vanderhoff, J. W., E. B. Bradford, M. L. Tarkowski, J. B. Schaffer, R. M. Wiley, *Ad. Chem. Ser.* 1962, 34, 32.
7. Baade, V., K. H. Reichert, *Eur. Polym. J.*, 1984, 20, 505.
8. Vanderhoff, J. W., F. V. Distefano, M. S. El Aasser, R. O'Leary, O. M. Schaffer, D. G. Visioli. *J. Dispers. Sci. Tech.*, 1984, 5, 323.
9. McHugh, M. A., V. J. Krukonis. *Supercritical Fluid Extraction*, Butterworths, Boston, 1986.
10. Fulton, J. L., R. D. Smith. *J. Phys. Chem.*, 1988, 92, 2903.
11. Kotlarchyk, M., S. Chen, J. S. Huang, M. W. Kim. *Phys. Rev. A* 1984, 29, 2054.
12. Windholz, M., S. Budavari, eds. *The Merck Index*, Tenth Ed., Merck and Co., Rahway, N.J., 1983.
13. Parrish, W. R., A. G. Pollin, T. W. Schmidt. *Proc. Sixty-First Ann. Conv., Gas Proc. Assoc.*, 1982, 164.
14. Leong, Y. S., F. Candau, G. Pouyet, S. J. Candau. *J Coll. Int. Sci.*, 1984, 101, 167.
15. Shinoda, K. S. Friberg. *Emulsions and Solubilization*, John Wiley and Sons, N.Y., 1986.
16. Griffin, W. C. *J. Soc. Cosmet. Chem.*, 1949, 1, 311.
17. Boyd, J. G. Parkinson, P. Sherman. *J. Coll. Int. Sci.* 1972, 41, 359.
18. Reynolds, W. C. *Thermodynamic Properties in SI*, Dept. of Mech. Eng., Stanford Univ., Stanford, Calif. 1979.
19. Matschke, D. E., G. Thodos. *J. Chem. Eng. Data* 1962, 7, 232
20. Schauber, C., & G. Riess. *Polym. Mat. Sci. Eng.* 1987, 57, 945.
21. Haque, E., & S. Qutubiddin. *Polym. Mat. Sci. Eng.* 1987, 57, 944.
22. Becher, P., in *Surfactants in Solution, Vol. III*, K. L. Mittal, B. Lindman, eds., Plenum Press, N.Y. 1983, p. 1925.
23. Wormuth, K. R. & E. W. Kaler, submitted to *J. Phys. Chem.*
24. Wormuth, K. R. & E. W. Kaler, *J. Phys. Chem.*, 1987, 91, 24.

TABLE 1
(see FIG. 1)

|   | AM = 0,T | AM = 0,P | AM = .25,T | AM = .25,P | AM = .33,T | AM = .33,P | AM = .4,T | AM = .4,P |
|---|---|---|---|---|---|---|---|---|
| 1 | 26.9 | 10.0 | 30 | 112.5 | 32.9 | 187.5 | 30 | 239 |
| 2 | 46.9 | 16.0 | 52 | 151 | 60.6 | 223 | 71.3 | 266 |
| 3 | 66.9 | 24 | 67.3 | 174 | 80.7 | 244.5 | | |
| 4 | 86.9 | 36 | 81.8 | 193 | 106.0 | 262 | | |
| 5 | | | 106.9 | 218 | | | | |

TABLE 8
(see FIG. 8)

|   | Phi = 0.098,T | Phi = 0.098,P | Phi = 0.094,T | Phi = 0.094,P | Phi = 0.118,T | Phi = 0.118,T | Phi = 0.163,T | Phi = 0.163,P |
|---|---|---|---|---|---|---|---|---|
| 1 | 30.3 | 411 | 29.8 | 437 | 31.3 | 355 | 31.2 | 327 |
| 2 | 35.8 | 443 | 33.6 | 463 | 37.8 | 375 | 35.9 | 337 |
| 3 | 41.0 | 481 | 36.7 | 487 | 45.0 | 398 | 43.5 | 350 |
| 4 | 46.4 | 539 | | | 51.9 | 423 | 51.2 | 364 |
| 5 | | | | | | | 58.4 | 380 |

Figure 9:
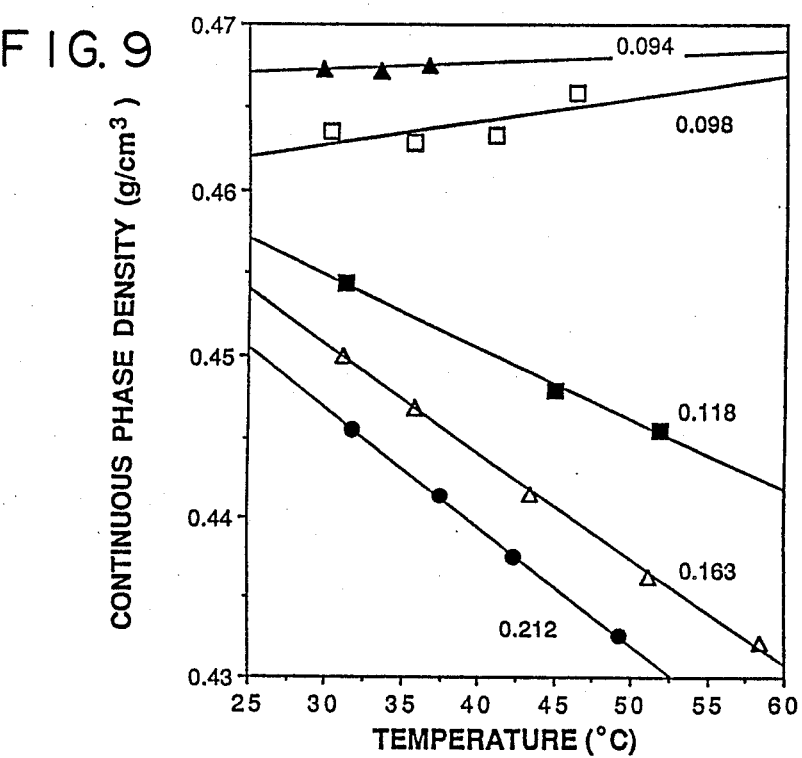
FIG. 9 is a graphical representation of the data from FIG. 10 replotted versus continuous phase density.
Figure 10:
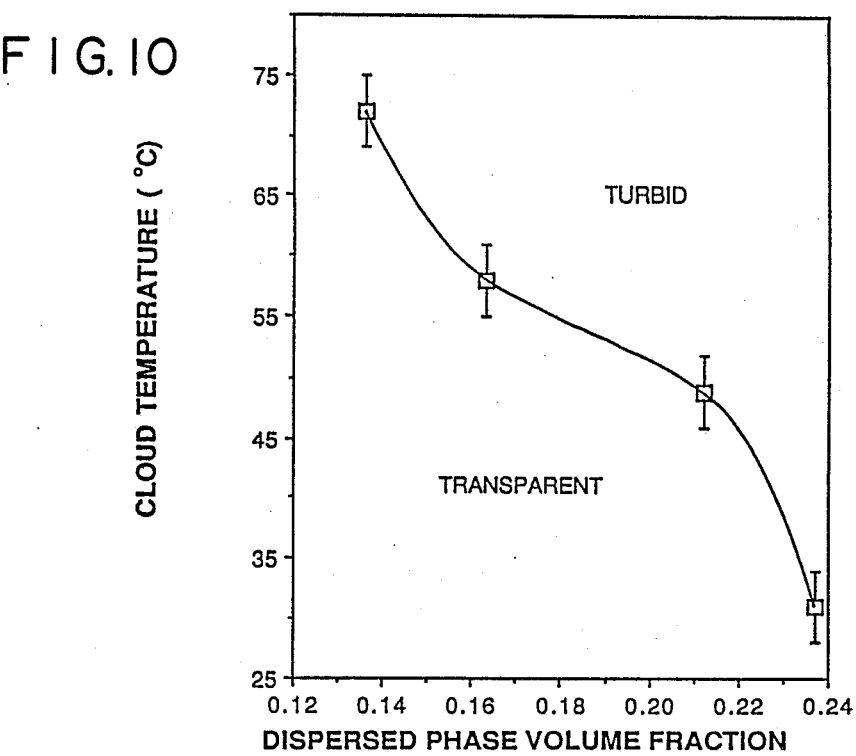
FIG. 10 is a graphical representation of the cloud point temperatures of non-ionic surfactant (B52/B30) mixtures in 80.4/19.6 supercritical fluid (ethane-propane) mixtures with a water/surfactant ratio of 5.0 and a monomer (acrylamide) to surfactant ratio of 1.0 versus dispersed phase volume fraction.

TABLE 9
(see FIG. 9)

|   | Phi = 0.212,T | Phi = 0.212,P | Phi = .098,rho | Phi = .094,rho | Phi = .118,rho | Phi = .163,rho | Phi = .212,rho |
|---|---|---|---|---|---|---|---|
| 1 | 31.8 | 305 | .46340 | .46724 | .45438 | .44999 | .44556 |
| 2 | 37.5 | 315 | .46274 | .46720 | .45119 | .44688 | .44134 |
| 3 | 42.4 | 322 | .46317 | .46752 | .44797 | .44146 | .43749 |
| 4 | 49.3 | 334 | .46583 | | .44552 | .43629 | .43258 |

TABLE 9-continued
(see FIG. 9)

| | Phi = 0.212,T | Phi = 0.212,P | Phi = .098,rho | Phi = .094,rho | Phi = .118,rho | Phi = .163,rho | Phi = .212,rho |
|---|---|---|---|---|---|---|---|
| 5 | | | | | | | .43214 |

NOTE:
T = °C.
P = bar
rho = continuous phase density
phi = volume fraction dispersed phase

Figure 2:
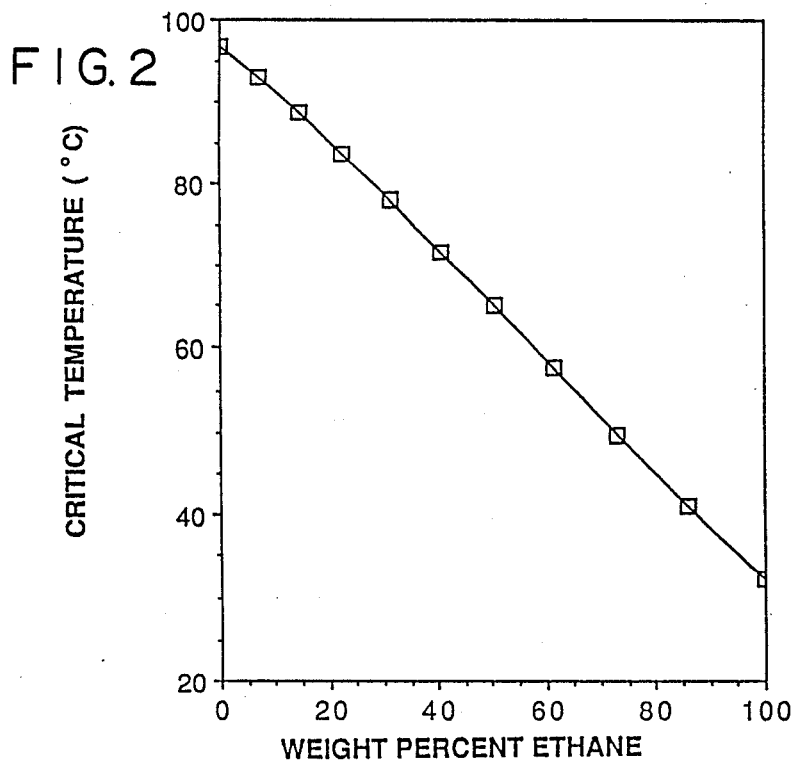
FIG. 2 is a graphical representation of the critical temperature of ethane/propane mixtures versus composition. (See Table 2 for data.)

TABLE 2
(see FIG. 2)

| | Wt % Ethane | $T_c$ (°C.) |
|---|---|---|
| 1 | 0.0 | 96.7 |
| 2 | 7.04 | 93.2 |
| 3 | 14.56 | 88.8 |
| 4 | 22.61 | 83.6 |
| 5 | 31.25 | 78.0 |
| 6 | 40.54 | 71.7 |
| 7 | 50.56 | 65.0 |
| 8 | 61.40 | 57.7 |
| 9 | 73.17 | 49.8 |
| 10 | 85.99 | 41.1 |
| 11 | 100.0 | 32.2 |

TABLE 6
(see FIG. 6)

| Max Water: Surfactant | Monomer: Surfactant |
|---|---|
| .25 | 0 |
| .50 | 3 |
| .75 | 4 |
| 1.00 | 6 |
| 1.25 | 8 |
| 1.50 | 7 |

TABLE 5
(see FIG. 5)

| | T,AM = 0.5 | P,AM = 0.5 | T,AM = 1.0 | P,AM = 1.0 | T,AM = 1.5 | P,AM = 1.5 |
|---|---|---|---|---|---|---|
| 1 | 27.0 | 103.4 | 25.3 | 132.4 | 28.5 | 162.7 |
| 2 | 33.4 | 123.4 | 33.5 | 155.5 | 35.5 | 185.1 |
| 3 | 39.6 | 141.7 | 39.5 | 171.3 | 41.7 | 205.5 |
| 4 | 46.3 | 160.3 | 42.7 | 179.6 | 47.9 | 227.2 |
| 5 | 52.2 | 178.6 | 45.4 | 187.5 | 53.7 | 251.0 |
| 6 | | | 50.8 | 202.4 | 60.0 | 283.4 |
| 7 | | | 56.1 | 217.9 | | |

NOTE:
T = °C.
P = bar

TABLE 7
(see FIG. 7)

| | Clearing Pressure (bar) | Volume Fraction Dispersal Phase |
|---|---|---|
| 1 | 0.094 | 437 |
| 2 | 0.098 | 411 |
| 3 | 0.118 | 355 |
| 4 | 0.137 | 340 |
| 5 | 0.163 | 327 |
| 6 | 0.188 | 303 |
| 7 | 0.212 | 305 |
| 8 | 0.237 | 310 |
| 9 | 0.277 | 305 |

Figure 3:
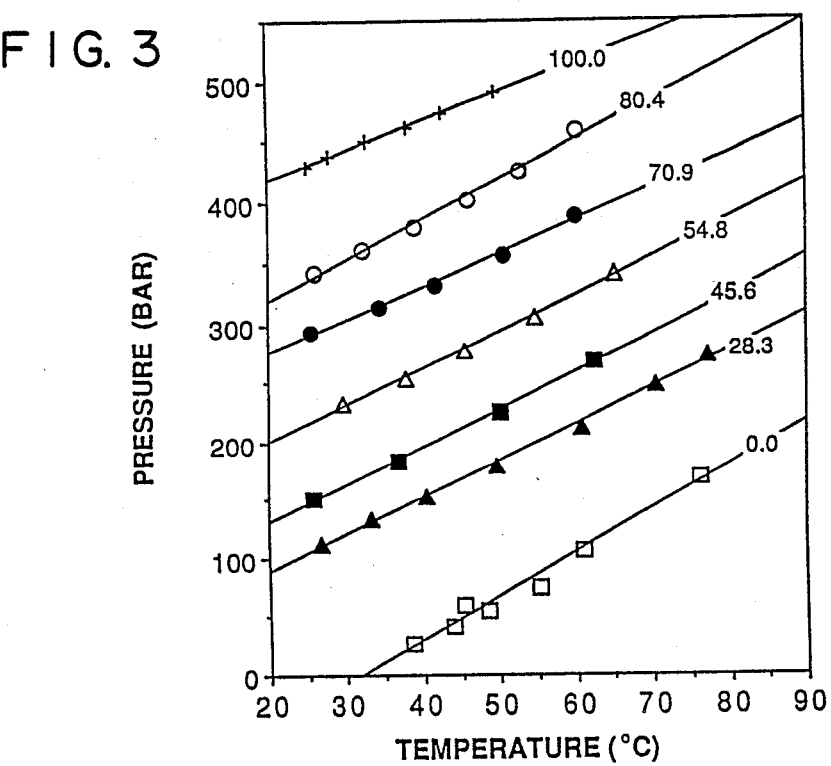
FIG. 3 is a graphical representation of cloud point curves of non-ionic surfactant (Brij 52 ("B52")/Brij 30 ("B30") 80/20 by weight mixtures, having a water to surfactant ratio of 5.0, a monomer (acrylamide) to surfactant ratio of 1.0, a total dispersed phase volume fraction of 0.136, at seven continuous phase ethane concentrations (weight %). (See Table 3 for data.)

TABLE 3
(see FIG. 3)

| | Temp 100% | Press 100% | Temp 72.7% | Press 71.7% | Temp 54.4% | Press 54.4% | Temp 45.2% | Press 45.2% |
|---|---|---|---|---|---|---|---|---|
| 1 | 45.3 | 59 | 26.8 | 112 | 25.8 | 150 | 29.7 | 232 |
| 2 | 61.1 | 106 | 33.2 | 132 | 37.0 | 184 | 37.9 | 253 |
| 3 | 76.2 | 169 | 40.6 | 152 | 50.1 | 225 | 45.7 | 277 |
| 4 | 38.6 | 27 | 49.7 | 179 | 62.5 | 268 | 54.8 | 306 |
| 5 | 43.8 | 42.4 | 60.8 | 212 | | | 65.1 | 341 |
| 6 | 48.4 | 55.5 | 70.4 | 247 | | | | |
| 7 | 55.2 | 75.2 | 77.2 | 273 | | | | |

| | Temp 29.1% | Press 29.1% | Temp 19.6% | Press 19.6% | Temp 0% | Press 0% |
|---|---|---|---|---|---|---|
| 1 | 25.6 | 294 | 26 | 343 | 25.1 | 430 |
| 2 | 34.4 | 314 | 32.3 | 360 | 27.9 | 438 |
| 3 | 41.7 | 332 | 39.1 | 378 | 32.9 | 450 |
| 4 | 50.6 | 356 | 46.1 | 401 | 38.2 | 461 |
| 5 | 60.0 | 388 | 52.9 | 425 | 42.8 | 473 |
| 6 | | | 60.4 | 457 | 49.8 | 491 |

NOTE:
T = °C.
Press = bar
% = % ethane

TABLE 4

Figure 4:
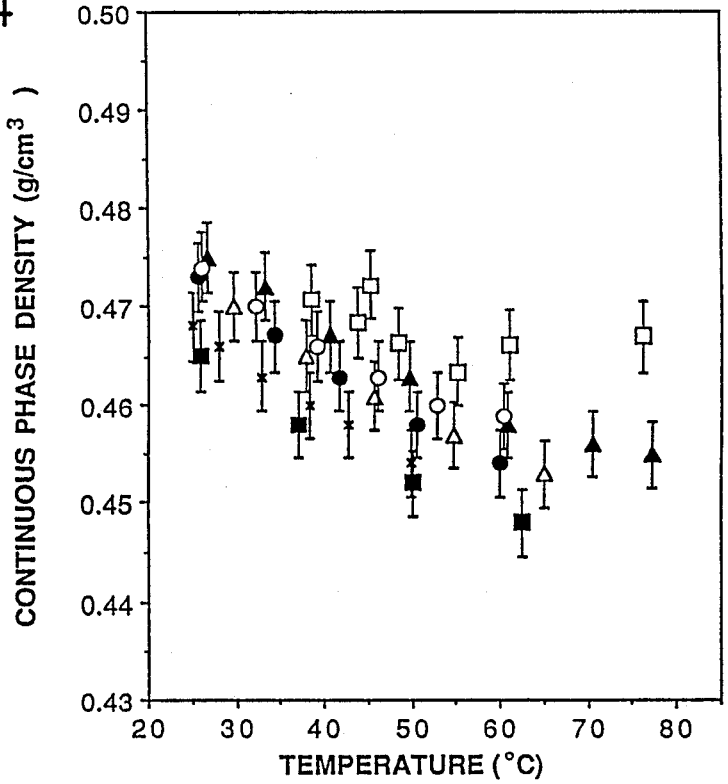
FIG. 4 is a graphical representation of data from FIG. 3 replotted as density of continuous phase at cloud point versus temperature; the symbols in FIG. 4 being the same as in FIG. 3. (See Table 4 for data.)

(see FIG. 4)

| | 100/0-T | 100/0-RHO | 71.7/28.3-T | 71.7/28.3-RHO | 54.4/45.6-T | 54.4/45.6-RHO | 45.2/54.8-T | 45.2/54.8-RHO | 29.1/70.9-T | 29.1/70.9-RHO |
|---|---|---|---|---|---|---|---|---|---|---|
| 1 | 38.6 | .4707 | 26.8 | .4593 | 25.8 | .4428 | 29.7 | .4543 | 25.6 | .4571 |
| 2 | 43.8 | .4684 | 33.2 | .4559 | 37.0 | .4428 | 37.9 | .4491 | 34.4 | .4513 |
| 3 | 45.3 | .4722 | 40.6 | .4514 | 50.1 | .4369 | 45.7 | .4454 | 41.7 | .4469 |
| 4 | 48.4 | .4663 | 49.7 | .4470 | 62.5 | .4333 | 54.8 | .4416 | 50.6 | .4423 |
| 5 | 55.2 | .4635 | 60.8 | .4423 | | | 65.1 | .4381 | 60.0 | .4389 |
| 6 | 61.1 | .4662 | 70.4 | .4406 | | | | | | |
| 7 | 76.2 | .4670 | 77.2 | .4399 | | | | | | |

| | 19.6/80.4-T | 19.6/80.4-RHO | 0/100-T | 0/100-RHO | 71.7, NEW RHO | 54.4, NEW RHO | 46.2, NEW RHO | 29.2, NEW RHO | 19.6, NEW RHO | 0, NEW RHO |
|---|---|---|---|---|---|---|---|---|---|---|
| 1 | 26.0 | .4578 | 25.1 | .4490 | 0.475 | 0.465 | 0.470 | 0.473 | 0.474 | 0.468 |
| 2 | 32.3 | .4542 | 27.9 | .4428 | 0.472 | 0.458 | 0.465 | 0.467 | 0.470 | 0.466 |
| 3 | 39.1 | .4504 | 32.9 | .4369 | 0.467 | 0.452 | 0.461 | 0.463 | 0.466 | 0.463 |
| 4 | 46.1 | .4474 | 38.2 | .4333 | 0.463 | 0.448 | 0.457 | 0.458 | 0.463 | 0.460 |
| 5 | 52.9 | .4449 | 42.8 | | 0.458 | | 0.453 | 0.454 | 0.460 | 0.458 |
| 6 | 60.4 | .4432 | 49.8 | | 0.456 | | | | 0.459 | 0.454 |
| 7 | | | | | 0.455 | | | | | |

NOTE:
T = °C.
Rho = continuous phase density
Weight % A/Weight % B = Propane/Ethane
New Rho = Adjusted continuous phase density Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

We claim:

1. A process for polymerizing a monomer which comprises
   forming a microemulsion comprising a first phase including a low-polarity fluid material which is a gas under standard temperature and pressure and has a cloud-point density, and a second phase including a polar fluid, a monomer substantially soluble in said polar fluid, and a microemulsion promoter for facilitating the formation of micelles including said monomer in said microemulsion;
   maintaining the system at a pressure and temperature such the density of the low-polarity fluid exceeds the cloud-point density thereof;
   forming micelles including said monomer in said microemulsion;
   introducing a polymerization initiator into the micelles in said microemulsion; and
   polymerizing said monomer in said micelles to produce a polymeric material.

2. The process of claim 1, wherein said first phase comprises a substantially continuous phase, said second phase comprises a substantially discontinuous phase, and said microemulsion comprises a substantially stable inverse emulsion.

3. The process of claim 1, wherein said polymerization is conducted at a temperature at least equal to the supercritical temperature of said fluid material.

4. The process of claim 2, wherein said monomer comprises a water-soluble monomer.

5. The process of claim 4, wherein said water-soluble monomer comprises at least one from the group consisting essentially of acrylamide, methacrylamide, acrylic acid, methacrylic acid, an acrylic acid salt, vinyl pyrolidone, and vinyl acetate.

6. The process of claim 1, wherein said microemulsion promoter comprises a surfactant which is substantially soluble in said first phase.

7. The process of claim 6, wherein the molar ratio of said water to said surfactant is at least about 5, and said surfactant substantially solubilizes said water at pressures up to 500 bar.

8. The process of claim 1, wherein said microemulsion promoter comprises at least one from the group consisting essentially of a non-ionic surfactant and an anionic surfactant.

9. The process of claim 8, wherein said surfactant has an HLB of from about 6 up to 8.

10. The process of claim 1, wherein said monomer acts as a microemulsion co-promoter in said second phase.

11. The process of claim 1, wherein said fluid material is at least one lower alkane.

12. The process of claim 1, wherein said lower alkane is at least one from the group consisting essentially of ethane, propane and butane.

13. The process of claim 2, wherein said polymerization initiator is capable of passing through said continuous phase and into said discontinuous phase for polymerizing said monomer in said micelles.

14. The process of claim 1, wherein said polymerization initiator is activated by at least one from the group consisting essentially of thermal and radiation means.

15. The process of claim 1, wherein said polymerization initiator comprises any one from the group consisting essentially of azo, peroxide, and disulfide initiator compounds.

16. The process of claim 1, wherein the pressure required to form said microemulsion is reduced as the amount of said second phase in said microemulsion is increased.

17. The process of claim 3, wherein the weight average molecular weight of said polymeric material polymerized at a temperature above the supercritical temperature of said fluid material is at least 25% greater than the weight average molecular weight of the polymeric material produced under substantially the same reaction conditions except that the polymerization is conducted at a temperature below the supercritical temperature of said fluid material.

18. A microemulsion comprising
a first phase including a low-polarity fluid material which is a gas under standard temperature and pressure and has a cloud-point density,
a second phase including a polar fluid, a monomer substantially soluble in said polar fluid, and a microemulsion promoter for facilitating the formation of micelles including said monomer in said microemulsion; and
micelles including said monomer in said microemulsion;
the system being maintained at a pressure and temperature such the density of the low-polarity fluid exceeds the cloud-point density thereof.

19. The process of claim 18, wherein said first phase comprises a substantially continuous phase, said second phase comprises a substantially discontinuous phase, and said microemulsion comprises a substantially stable inverse emulsion.

20. The process of claim 18, wherein said monomer comprises at least one from the group consisting essentially of acrylamide, methacrylamide, acrylic acid, methacrylic acid, an acrylic acid salt, vinyl pyrolidone, and vinyl acetate.

21. The process of claim 18, wherein said microemulsion promoter comprises a surfactant which is substantially soluble in said second phase.

22. The process of claim 18, wherein the molar ratio of said surfactant to said water is at least about 1:5, and said surfactant substantially solubilizes said water at pressures up to 500 bar.

23. The process of claim 18, wherein said microemulsion promoter comprises at least one from the group consisting essentially of a non-ionic surfactant and an anionic surfactant.

24. The process of claim 23, wherein said surfactant has an HLB of from about 5 up to 10.

25. The process of claim 18, wherein said monomer acts as a microemulsion co-promoter in said second phase.

26. A process for polymerizing a water-soluble monomer which comprises
forming a substantially stable inverse microemulsion comprising a first substantially discontinuous phase including a fluid material which is either one of a gas under ambient conditions and a liquified gas, and a substantially continuous second phase including water, a water-soluble monomer, and a surfactant which is substantially soluble in said second phase for facilitating the formation of micelles including said monomer in said microemulsion;
forming micelles including said monomer in said microemulsion;
introducing a polymerization initiator capable of passing through said continuous phase and into said micelles of said discontinuous phase; and
polymerizing said monomer in said micelles to produce a polymeric material.

27. The process of claim 26, wherein said polymerization is conducted at a temperature at least equal to the supercritical temperature of said fluid material.

28. The process of claim 26, wherein said water-soluble monomer comprises at least one from the group consisting essentially of acrylamide, methacrylamide, acrylic acid, methacrylic acid, an acrylic acid salt, vinyl pyrolidone, and vinyl acetate.

29. The process of claim 26, wherein the molar ratio of said surfactant to said water is at least about 5, and said surfactant substantially solubilizes said water at pressures up to 500 bar.

30. The process of claim 26, wherein said surfactant comprises at least one from the group consisting essentially of a non-ionic surfactant and an anionic surfactant.

31. The process of claim 26, wherein said surfactant has an HLB of from about 5 up to 10.

32. The process of claim 26, wherein said monomer acts as a co-surfactant in said second phase.

33. The process of claim 26, wherein said fluid material is at least one lower alkane.

34. The process of claim 26, wherein said polymerization initiator is activated by at least one from the group consisting essentially of thermal and radiation means.

35. The process of claim 26, wherein the pressure required to form said microemulsion is reduced as the amount of said second phase in said microemulsion is increased.

36. The process of claim 26, wherein the weight average molecular weight of said polymeric material polymerized at a temperature above the supercritical temperature of said fluid material is at least 25% greater than the weight average molecular weight of the polymeric material produced under substantially the same reaction conditions except that the polymerization is conducted at a temperature below the supercritical temperature of said fluid material.

37. The process of claim 1, wherein the polymerization is conducted at a temperature up to the temperature that the microemulsion promoter will be thermally destroyed.

38. The process of claim 37, wherein said polymerization temperature is up to about 120° C.

39. The process of claim 26, wherein the polymerization is conducted at a temperature up to the temperature that the microemulsion promoter will be thermally destroyed.

40. The process of claim 39, wherein said polymerization temperature is up to about 120° C.

* * * * *

UNITED STATES PATENT AND TRADEMARK OFFICE
CERTIFICATE OF CORRECTION

PATENT NO. : 4,933,404

DATED : June 12, 1990

INVENTOR(S) : Eric J. Beckman & Richard D. Smith

It is certified that error appears in the above-identified patent and that said Letters Patent is hereby corrected as shown below:

Table 4,    Second column heading line, change "46.2 NEW RHO" to -- 45.2, NEW RHO--.

Signed and Sealed this

Third Day of March, 1992

Attest:

HARRY F. MANBECK, JR.

*Attesting Officer*    *Commissioner of Patents and Trademarks*

UNITED STATES PATENT AND TRADEMARK OFFICE
CERTIFICATE OF CORRECTION

PATENT NO. : 4,933,404

DATED : June 12, 1990

INVENTOR(S) : Eric J. Beckman; Richard D. Smith; and John L. Fulton

It is certified that error appears in the above-identified patent and that said Letters Patent is hereby corrected as shown below: <u>Col. 11 & 12:</u>

Table 3, in the column heading line: Change "Press 71.7%" to --72.7%--.

Claims 19-23 and 25, first line: Change "process" to --microemulsion--.

Signed and Sealed this

Twenty-first Day of September, 1993

Attest:

BRUCE LEHMAN

Attesting Officer

Commissioner of Patents and Trademarks